United States Patent [19]

Martakos et al.

[11] Patent Number: 5,474,824
[45] Date of Patent: Dec. 12, 1995

[54] PROCESS FOR EXPANDING POLYTETRAFLUOROETHYLENE AND PRODUCTS PRODUCED THEREBY

[75] Inventors: Paul Martakos, Pelham; Theodore Karwoski, Hollis; Steve A. Herweck, Nashua, all of N.H.

[73] Assignee: Atrium Medical Corporation, Hudson, N.H.

[21] Appl. No.: 268,240

[22] Filed: Jun. 29, 1994

Related U.S. Application Data

[63] Continuation of Ser. No. 850,862, Mar. 13, 1992.

[51] Int. Cl.[6] .................................................. A61F 2/06
[52] U.S. Cl. .................... 428/36.9; 428/36.92; 428/131; 428/317.9; 428/319.1; 428/319.7; 428/422; 623/1; 623/11
[58] Field of Search ..................... 623/1, 11; 428/422, 428/317.9, 319.1, 319.7, 131, 36.9, 36.92

[56] References Cited

U.S. PATENT DOCUMENTS

| | | | |
|---|---|---|---|
| 3,953,566 | 4/1976 | Gore | 264/288 |
| 4,082,893 | 4/1978 | Okita | 428/376 |
| 4,104,394 | 8/1978 | Okita | 264/89 |
| 4,177,334 | 12/1979 | Okita | 521/145 |
| 4,187,390 | 2/1980 | Gore | 174/102 |
| 4,208,745 | 6/1980 | Okita | 3/1.4 |
| 4,225,547 | 9/1980 | Okita | 264/127 |
| 4,234,535 | 11/1980 | Okita | 264/519 |
| 4,250,138 | 2/1981 | Okita | 264/568 |
| 4,277,429 | 7/1981 | Okita | 264/17 |
| 4,283,448 | 8/1981 | Bowman | 428/36 |
| 4,355,426 | 10/1982 | MacGregor | 3/1.4 |
| 4,385,093 | 5/1983 | Hubis | 428/316 |
| 4,482,516 | 11/1984 | Bowman et al. | 264/127 |
| 4,596,837 | 6/1986 | Yamamoto et al. | 521/145 |
| 4,598,011 | 7/1986 | Bowman | 428/211 |
| 4,647,416 | 3/1987 | Seiler, Jr. et al. | 264/118 |
| 4,687,482 | 8/1987 | Hanson | 623/1 |
| 4,743,480 | 5/1988 | Campbell et al. | 428/36 |
| 4,760,102 | 7/1988 | Moriyama et al. | 521/145 |
| 4,816,339 | 3/1989 | Tu et al. | 428/421 |
| 4,820,787 | 4/1989 | Kataoka et al. | 526/255 |
| 4,822,352 | 4/1989 | Joh et al. | 623/1 |
| 4,822,361 | 4/1989 | Okita et al. | 623/12 |
| 4,824,898 | 4/1989 | Sukigara et al. | 524/401 |
| 4,876,051 | 10/1989 | Campbell et al. | 364/127 |

(List continued on next page.)

OTHER PUBLICATIONS

"Tetrafluoroethylene Polymers;" Enc. of Poly. Sci. & Eng., vol. 16 pp. 582–583 Wiley and Sons 1989.
"Tailoring the Negative Poisson Ratio;" Ken Evans, Chemistry & Industry, 15 Oct. 1990; pp. 654–657.
"Microporous Materials with Negative Poisson's ratios": II. Mechanisms and Interpretation; K. E. Evans & B. D. Caddock J. Phys. D: Appln. Phys. 22(1989) pp. 1883–1887.
"Microporous Materials With Negative Poisson's Ratios: I. Microstructure and Mechanical Properties;" B. D. Caddock and K. E. Evans; J. Phys. D: Appl. Phys. 22 (1989) pp. 1877–1882.

Primary Examiner—James J. Seidleck
Assistant Examiner—Michael A. Williamson

[57] ABSTRACT

A process for producing a shaped porous article includes the steps of providing an extrudate of a fluoropolymer material which is capable of being stretched and bilaterally stretching the extrudate along a longitudinal axis. The stretching step is carried out under conditions sufficient to yield an article which is substantially uniformly stretched over a major portion of its length. After stretching, the material has a unique through-pore microstructure characterized by elongate nodes connected by fibrils. The stretched material is sintered while being maintained in its stretched state to produce the shaped porous article. A significant feature of the inventive process is that stretching is carried out by displacing both ends of the extruded material as opposed to known method wherein only one end of an extruded material is stretched, resulting in a microporous fluoropolymer article which are different than conventional fluoropolymer stretching/expansion processes.

19 Claims, 5 Drawing Sheets

U.S. PATENT DOCUMENTS

| | | | |
|---|---|---|---|
| 4,902,508 | 2/1990 | Badylak et al. | 424/95 |
| 4,973,609 | 11/1990 | Browne | 521/81 |
| 5,026,513 | 6/1991 | House et al. | 264/127 |
| 5,071,610 | 12/1991 | Hagen et al. | 264/120 |
| 5,098,625 | 3/1992 | Huang et al. | 264/127 |
| 5,098,779 | 3/1992 | Kranzler et al. | 428/306.6 |
| 5,102,921 | 4/1992 | Harada et al. | 521/134 |
| 5,110,526 | 5/1992 | Hayashi et al. | 264/127 |
| 5,110,527 | 5/1992 | Harada et al. | 264/127 |

PROCESS FOR EXPANDING POLYTETRAFLUOROETHYLENE AND PRODUCTS PRODUCED THEREBY

This application is a continuation of application Ser. No. 07/850,862, filed on Mar. 13, 1992.

BACKGROUND OF THE INVENTION

Many fluoropolymer materials, such as polytetrafluoroethylene (PTFE), are thermoplastic polymers. That is, they have the property of softening when heated and of hardening again when cooled. PTFE is generally produced in the form of white powder referred to as resin. It has a higher crystalline melting point (327° C.) and higher viscosity than other thermoplastic polymers, which makes it difficult to fabricate in the same manner as other plastics.

PTFE is a long chain polymer composed of $CF_2$ groups. The chain length determines molecular weight, while chain orientation dictates crystallinity. The molecular weight and crystallinity of a given resin prior to sintering are controlled by the polymerization process.

Currently, three different types of PTFE resins are available which are formed from two different polymerization processes. The three resins are granular polymer, aqueous dispersions, and coagulated dispersion products.

In the coagulated dispersion of PTFE resin, small diameter (0.1–0.2 micrometer) particles are coagulated under controlled conditions to yield agglomerates ranging in size from 400 to 500 micrometers in diameter. The morphological structure of these agglomerates can be considered as long chains of PTFE that are intermingled in a tangled network.

A known method of forming articles from fluoropolymer resins, such as PTFE, is to blend a resin with an organic lubricant and compress it under relatively low pressure into a preformed billet. Using a ram type extruder, the billet is then extruded through a die in a desired cross-section. Next, the lubricant is removed from the extruded billet by drying or other extraction method. The dried extruded material (extrudate), is then rapidly stretched and/or expanded at elevated temperatures below the crystalline melting point of the resin. In the case of PTFE, this results in the material taking on a microstructure characterized by elongated nodes interconnected by fibrils. Typically, the nodes are oriented with their elongated axis perpendicular to the direction of stretch.

After stretching, the porous extrudate is sintered by heating it to a temperature above its crystalline melting point while it is maintained in its stretched condition. This can be considered as an amorphous locking process for permanently "locking-in" the microstructure in its expanded or stretched configuration.

It has been found that the effect caused by stretching PTFE is dependent on extrudate strength, stretch temperature, and stretch rate. Extrudate strength is a function of the molecular weight and degree of crystallinity of the starting resin and extrusion conditions such as extrusion pressure, lubricant level, and reduction ratio. These parameters also control the degree of alignment that results from extrusion. As stated, the degree of alignment, in turn, affects one's ability to homogeneously stretch the extrudate.

Most known methods for processing PTFE describe unilateral stretching techniques and stress the importance of stretching the fluoropolymer at rapid rates. For example, U.S. Pat. Nos. 3,953,566 and 4,187,390 to Gore state that while there is a maximum rate of expansion beyond which fracture of the material occurs, the minimum rate of expansion is of much more practical significance. Indeed, the patents state that at high temperatures within the preferred range for stretching (35° C.–327° C.) only the lower limit of expansion rate has been detected. The patents estimate this rate to be ten percent of the initial length of the starting material per second. The patents go on to note that the lower limit of expansion rates interact with temperature in a roughly logarithmic fashion so that at higher temperatures within the preferred stretching range, higher minimum expansion rates are required.

U.S. Pat. No. 4,973,609 to Browne describes another method for producing porous PTFE products by stretching at a rate of 10% per second. The patent also states that a differential structure is obtained by using an alloy of two different fluoropolymer resins which are characterized by significantly different stretch characteristics. The resins typically have different molecular weights and/or crystallinities. Accordingly, the final physical properties, such as strength, of PTFE articles formed in such a way are affected by the different molecular weights and/or crystallinities of the starting resins.

U.S. Pat. Nos. 4,208,745 and 4,713,070 also describe methods for producing porous PTFE products having a variable structure. The processes utilize a sintering step having a differential sintering profile. That is, one surface of an expanded PTFE article is sintered at a temperature which is higher than the sintering temperature of another surface. This results in fibrils being broken and provides an inherently weak material.

SUMMARY OF THE INVENTION

It is an object of the invention to provide a process for producing a shaped porous article which is more truly semi-permeable than known articles formed of fluoropolymer materials. It is another object of the invention to provide such a process in which a fluoropolymer extrudate can be homogeneously stretched independently of rate. Still another object is to provide a porous article. Yet another object of the invention is to provide a porous article having a porosity which is variable in the direction of the article's cross-section.

These and other objects are achieved by the present invention which in one aspect features a process for producing a porous article. The process includes the steps of providing an extrudate of a fluoropolymer material which is capable of being stretched and bilaterally stretching the extrudate along its longitudinal axis. Conditions are maintained during stretching sufficient to yield an article which is substantially uniformly stretched over a major portion of its length. These conditions include stretch rate, ratio, and temperature.

The stretched extrudate has a microstructure which is characterized by elongate nodes which are connected by fibrils. This microstructure is locked in by sintering the stretched extrudate while maintaining it in its stretched state.

An important feature of the invention is that the fluoropolymer extrudate is bilaterally stretched. That is, in accordance with the invention both ends of the extrudate are displaced along the extrudate's longitudinal axis away from a central portion of the extrudate. It has been found that this stretching method provides significant advantages over known stretching methods wherein one end of an extrudate is held stationary while only the other end is displaced.

In various embodiments of this aspect of the invention the bilateral stretching is carried out at rates not greater than ten percent per second. Indeed, it has been found that stretching at rates slower than even one percent per second provides a material having an extremely desirable microstructure of nodes and fibrils, the nodes being significantly larger than nodes resulting from known processes of rapidly stretching single-resin extrudates unilaterally.

In carrying out the stretching step in accordance with the process of the invention, the ends of the extrudate can be displaced either simultaneously or sequentially. For example, in one embodiment of the invention, a first end of the extrudate is displaced to a stretch ratio of not greater than two to one. That first end is then held stationary while the second end of the extrudate is displaced in the opposite direction to again result in a stretch ratio of not greater than two to one. Restricting the individual stretches to stretch ratios of not greater than two to one ensures a substantially homogeneous microstructure along a major portion the length of the extrudate.

In another aspect, the invention features a process for producing a porous tube of polytetrafluoroethylene including the step of providing a preformed billet of a mixture of a polytetrefluoroethylene resin and a lubricant. As with the above-described aspect of the invention, the billet is extruded, the extrudate is then dried, and bilaterally stretched along its longitudinal axis under conditions sufficient to yield a tube having a substantially homogenous microstructure over a major portion of its length. The stretched tube is then sintered while being maintained in its stretched state to produce the porous tube.

In one embodiment of this aspect of the invention, the preformed billet is formed to have a lubricant level which selectively varies in the direction of the billet's cross-section. That is, for example, the billet might have a lubricant level of fifteen percent by weight at its inner and outer surfaces and a lubricant level of approximately twenty percent at a radial position between its inner and outer surfaces. When extruded and stretched, such a billet results in a porous tube having a microstructure which varies in a controlled fashion in the direction of the tube's cross-section. This phenomenon and its advantages are described below in greater detail.

Accordingly, in the various embodiments of this aspect of the invention, a porous article having a desired microstructure is provided by controlling the billet lubricant level, the billet reduction ratio, and bilateral stretching conditions such as stretch rate and ratio. This avoids the problems such as weak material which are associated with known resin-blending and varied-profile sintering techniques.

In still another aspect, the invention features a tube formed of an expanded porous fluoropolymer material. The material has a microstructure characterized by ring shaped nodes interconnected by fibrils. An important feature of this aspect of the invention is that substantially all of the nodes each circumscribes the longitudinal axis of the tube and extends from the inner to the outer surface of the tube wall, thereby creating between the nodes continuous through-pores from one surface to the opposite surface.

These and other features of the invention will be more fully appreciated by reference to the following detailed description which is to be read in conjunction with the attached drawings.

DETAILED DESCRIPTION

Figure 1:
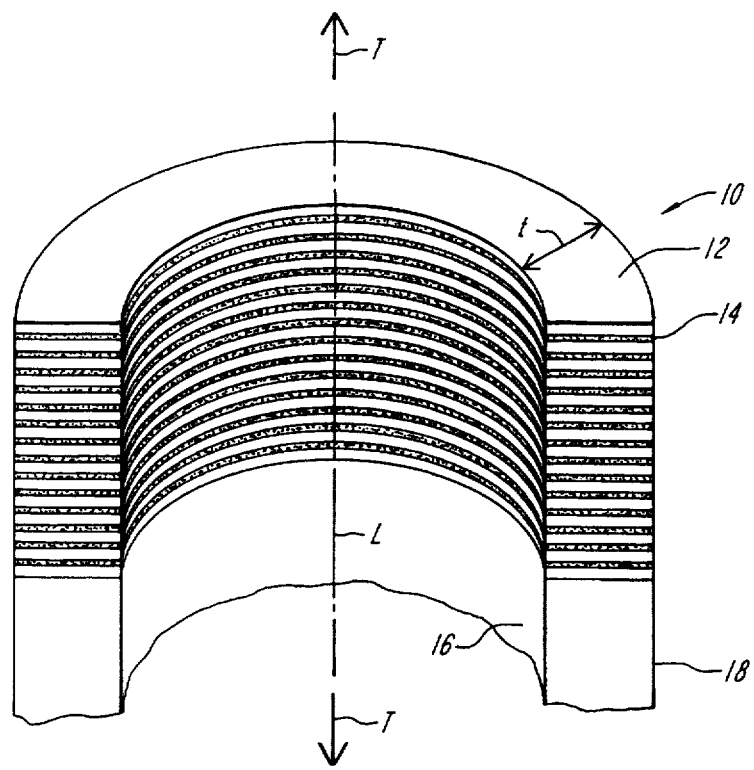
FIG. 1 is a schematic representation of a porous article formed in accordance with the teachings of the present invention.

As stated above, in one aspect the invention features a process for producing a shaped porous article. A significant feature of the process is that an article having a homogeneous microstructure is formed independently of the rate at which it is stretched.

Various fluoropolymer resins are suitable for use in the present invention. For example, polytetrafluoroethylene or copolymers of tetrafluoroethylene with other monomers may be used. Such monomers may be ethylene, chlorotrifluoroethylene, perfluoroalkoxytetrafluoroethylene, or fluorinated propylenes such as hexafluoropropylene. In particular, however, polytetrafluoroethylene (PTFE) works well. Accordingly, while the inventive process can be utilized to produce porous articles formed of various fluoropolymer materials, the following description pertains specifically to the formation of an article from PTFE resin.

For purposes of the present invention, when PTFE is used, resin of a molecular weight between 10,000,000 and 70,000,000 is suitable. Since, however, PTFE does not dissolve in any common solvent its molecular weight cannot be measured by the usual methods. According to the *Encyclopedia of Polymer Science and Engineering* (Wiley and Sons, 1989), though, the following relationship has been established between number-average molecular weight (Mn), for molecular weights between $5.2 \times 10^5$ and $4.5 \times 10^7$, and the heat of crystallization ($\Delta$Hc) in Joules/gram (calories/gram).

$$Mn = (2.1 \times 10^{10}) \times \Delta Hc^{-5.16}$$

Accordingly, by determining the heat of crystallization of a given PTFE resin, a number average molecular weight of the resin is determinable from this relationship.

As with known methods of processing PTFE, the invention utilizes a preformed billet which comprises a PTFE resin mixed with an organic lubricant. Various lubricants are suitable such as naphtha, ISOPAR-G and ISOPAR-H available from Exxon Corporation. Low odor paraffin solvents can be used as well. The blended resin is compressed at low pressure (less than 1000 PSI) into a tubular billet of approximately one third of the resin's original volume. Billet forming processes are generally known in the art.

As discussed above, extrusion conditions have a significant effect on the resulting extrudate's reaction to being stretched. In particular, once a resin of a given molecular weight and crystallinity has been selected, extrudate qualities are controlled by the level of lubricant mixed with the resin to form the billet, the reduction ratio at which the billet is extruded and the extrusion pressure. This is because these parameters control the degree to which the molecular chains of PTFE align themselves during extrusion.

The process of the invention is most effective when using lubricant levels that are higher than conventionally used in known methods for processing fluoropolymer materials. For example, preformed billets ranging in lubricant level of between 15 to 25 percent by weight produce an extrudate well adapted for the inventive stretching process. This is because higher lubricant levels facilitate the migration of molecular chains during the extrusion process to produce an extrudate having a higher degree of alignment. As discussed above, the degree of alignment in turn affects how the extrudate reacts to being subjected to an external tensile force.

When PTFE extrudate is subjected to an external tensile force, such as during stretching, the intermingled network of PTFE particles separate. Accordingly, the force required to separate these particles, and hence stretch the extrudate, is dependent upon the degree of intermingling of the PTFE particles. The longer the polymer chains (higher molecular weight), the greater the amount of intermingling that will occur and, therefore, the greater the force that will be required to separate the coagulated dispersion particles.

Two other extrusion parameters having an effect on a resulting extrudate's reaction to stretching are reduction ratio and extrusion pressure. The range of suitable reduction ratios is bounded at its lower end by the minimum reduction ratio permissible which provides an extrudate of sufficient strength so as not break during stretching. At its upper limit, the range of suitable reduction ratios is bounded by the maximum ratio permissible which provides an extrudate that is amenable to being homogeneously stretched. Accordingly, experimentation has shown that for purposes of the present invention the preformed billet should be extruded to a reduction ratio of between approximately 50:1 and 600:1. A preferred reduction ratio is between approximately 100:1 and 200:1.

Reduction ratio and stretch characteristics are interrelated since the force required to deform a PTFE extrudate and form fibrils from the nodes is related to how the material was aligned (packing density) during extrusion. Fibrils are not formed as easily from nodes with high reduction ratio extrudates as they are with low reduction ratio extrudates. This is because internal forces are much higher in high reduction ratio extrudates.

The third extrusion parameter which has a significant effect on the resulting extrudate's reaction to being stretched is extrusion pressure. While extrusion pressure is, to a certain extent, related to reduction ratio, by varying lubricant level, extrusion pressure can be varied independently of reduction ratio. While measured extrusion pressure will vary depending upon the type of extrusion equipment being used, the range of suitable extrusion pressures to practice the present invention will be apparent to those skilled in the art. For example, pressures between approximately 6000 PSI and approximately 10,000 PSI have been used successfully for the practice of the invention.

Once an extrudate has been produced according to the above described parameters, in accordance with the inventive process it is stretched under conditions sufficient to yield an article that is uniform over a major portion of its length. Stretching processes are characterized in terms of stretch rate and stretch ratio. Stretch rate refers to the percentage change in length of the extrudate per unit time. In the case of a fifty centimeter long extruded tube, for example, stretching five centimeters per second results in a stretch rate of ten percent per second. The percentage change is calculated in terms of the initial length of the extrudate.

Stretch ratio, on the other hand, is not time dependent but merely refers to the ratio of the final length of the stretched extrudate to that of the initial length of the unstretched extrudate. Accordingly, stretching a fifty centimeter long extruded tube to one hundred centimeters, results in a stretch ratio of 2:1 regardless of the duration of the stretch.

With this in mind, it is an important feature of the invention that extruded materials are stretched to form porous articles independently of stretch rate. In certain instances the process is dependent on stretch ratio. As stated above, known methods for processing fluoropolymer materials teach that stretching must be carried out at a rate generally exceeding approximately ten percent per second. In accordance with the invention, however, homogeneous articles are produced at stretch rates not greater than approximately ten percent per second. Indeed, the preferred rate of stretching ranges from approximately 0.5 percent per second to approximately 10 percent per second.

To stretch an extrudate, the extrudate must be placed in tension. This is done by applying opposed forces to the ends of the extrudate. The level of force applied to the extrudate, and hence the rate at which the extrudate stretches, determines how the above-described intermingled network of PTFE particles unravels. In known methods for stretching PTFE, force is applied to place the extrudate in tension by displacing one end of the extrudate with respect to the other end. At stretch rates lower than ten percent per second, this method of stretching cannot uniformly stretch the extrudate to greater than a 2:1 ratio. To the contrary, at greater ratios the material stretches preferentially at its moving end. The fixed end of the material, on the other hand, experiences significantly less stretching.

In accordance with the invention, on the other hand, bilateral stretching results in more even force distribution along the length of the extrudate and produces a more homogeneously stretched material. It has been found that stretching bilaterally, that is, displacing both ends of the extrudate away from the middle of the extrudate, provides a material that is homogeneously stretched over the majority of its length independent of the stretch rate.

After the extrudate has been bilaterally stretched it is sintered by heating it above its crystalline melting point under tension. As discussed above, this locks in the microstructure of the material and completes the process of producing the porous article.

FIG. 1 is a schematic representation of a porous tube 10 formed by the above described bilateral stretching process. For purposes of description, the microstructure of the tube 10 has been exaggerated. Accordingly, while the dimensions of the microstructure are enlarged, the general character of the illustrated microstructure is representative of that microstructure prevailing in an article formed by the inventive process.

Accordingly, the tube 10 includes a microstructure characterized by elongate nodes 12 interconnected by fibrils 14. A significant feature of the tube 10 is that the nodes 12 are ring-shaped to form, in effect, a series of washer type structures circumscribing the tube's longitudinal axis L. The nodes 12 are oriented generally perpendicularly to the axis of stretching as represented by arrows T which is coincident with the longitudinal axis L.

Another significant feature of the tube's microstructure is that substantially all of the nodes 12 extend along a transverse axis t from an inner surface 16 of the tube to an outer surface 18 of the tube. Accordingly, this dimension of the nodes 12 is significantly larger than the corresponding dimension of nodes formed by conventional single-resin fluoropolymer processing methods. Such nodes are randomly arranged and characterized by a transverse axis which is generally oriented perpendicularly to the axis of stretch. Notably, however, the nodes of these known structures are considerably shorter and smaller than nodes produced in accordance with the present invention. Indeed, the above-referenced U.S. patents to Gore note that nodes formed by that known technique generally range in size from smaller than one micron to approximately 400 microns.

Unlike the short, randomly stacked nodes and microfibrillar spaces formed by conventional single-resin fluoropolymer stretch or expansion processing, the method of the present invention provides a microporous structure having microfibrillar spaces which define through-pores or channels extending entirely from the inner to the outer wall of the expanded extrudate. These through-pores are perpendicularly oriented internodal spaces which traverse from one surface to another. As discussed below in greater detail, by varying lubricant levels such internodal through-pores can be preferentially altered such that the surface pore on one surface is made to be larger or smaller than the surface pore on the opposing surface.

Figure 2:
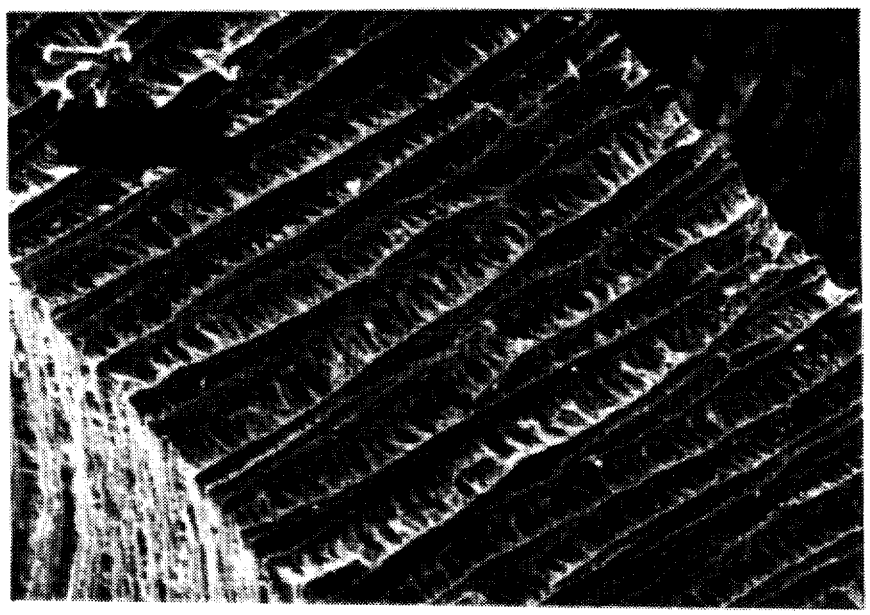
FIG. 2 is a scanning electron microscopic view of a longitudinal cross-section of a porous article in accordance with the invention.

A longitudinal cross-section view of a tubular article formed by the process of the invention is shown in FIG. 2. There, it can be seen that the present invention produces an article having a microstructure characterized by elongate nodes which are substantially larger than the nodes of materials produced by known single-resin forming methods. Indeed, the nodes shown in FIG. 2 consistently range in size from approximately 500 microns to approximately 900 microns. Substantially all of the nodes of the article shown in FIG. 2 extend from the inner surface of the tubular article to the outer surface of the tubular article, thereby creating through-pores substantially all of which traverse from one surface of the article to the other.

Figure 3:
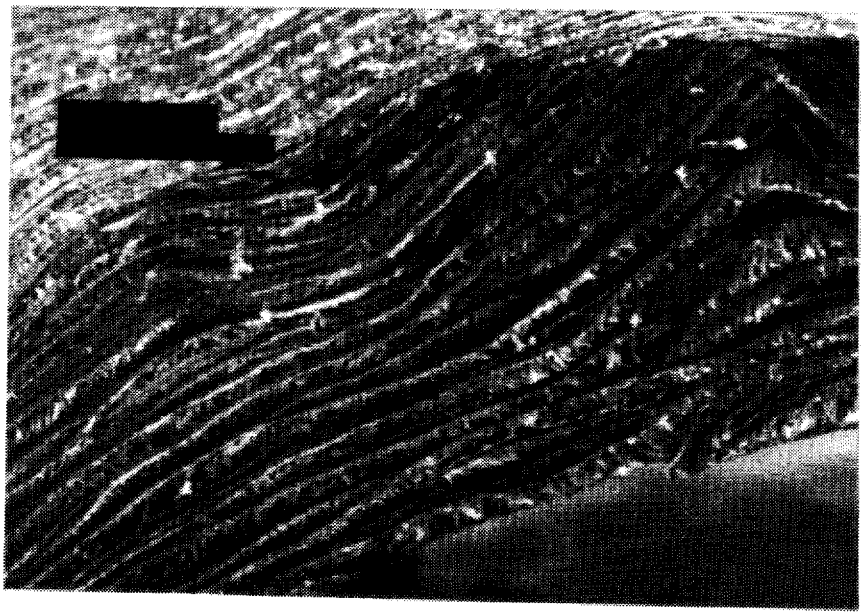
FIG. 3 is a scanning electron microscopic view of a radial cross-section of a porous article in accordance with the invention.

FIG. 3 is a radial cross-section view of the tubular article shown in FIG. 2. There it can be seen that while the nodes are generally oriented perpendicularly to the axis of stretch, as represented in FIG. 1, they are not perfectly flat and, therefore, a radial cross-section cuts through many nodes. Accordingly, while the schematic representation in FIG. 1 is useful for purposes of explanation, the scanning electron microscope photographs in FIGS. 2 and 3 are truer depictions of a product produced by the inventive process.

Products provided by the invention are suitable for a wide range of biological applications such as for vessel implants or organ wall grafts. In particular, as described below, vascular grafts formed by the process of the invention enjoy various advantages. Indeed, the processes of the invention are well suited for the formation of the various biological devices described in the following commonly assigned and co-pending U.S. patent applications: U.S. Ser. No. 760,753 for "IMPLANTABLE PROSTHETIC DEVICE FOR THE DELIVERY OF A BIOACTIVE MATERIAL"; U.S. Ser. No. 760,716 for "MANUALLY SEPARABLE MULTI-LUMEN VASCULAR GRAFT"; U.S. Ser. No. 760,728 for "IMPLANTABLE PROSTHETIC DEVICE HAVING INTEGRAL PATENCY DIAGNOSTIC INDICIA"; U.S. Ser. No. 760,717 for "POLYLUMENAL IMPLANTABLE ORGAN"; and U.S. Ser. No. 760,718 for "SELF-SEALING IMPLANTABLE VASCULAR GRAFT" all of which were filed 16 Sep. 1991. The specifications of these applications for patent are hereby incorporated herein by reference.

As stated, several structural, clinical and biological advantages accrue from the microstructure engendered by the inventive process. For example, as discussed below in greater detail with regard to the various examples, larger node size provides a structure having a significantly improved radial tensile strength. Also, tubes formed by the inventive process have improved burst pressure and suture strength characteristics. The flat ring-like node structure imparts significantly more flexibility, without kinking, than conventional fluoropolymer processes, in addition to providing superior resistance to radial twist compression or "torque twist." The tubular article formed by the process of the invention allows a significant degree of bending or radial twist, before experiencing lumen collapse or kinking, unlike conventional fluoropolymer articles which exhibit significantly less resistance to "torque twist" or "bending." Conventional articles, therefore, kink under smaller stress loads than do the articles of the current invention.

Additionally, the method of the current invention produces articles which exhibit significantly more simple compression resistance than conventionally processed articles. This provides more resistance to luminal collapse under equivalent stress loads. The articles provided by the invention also exhibit increased flexibility for enhanced drapability, or ability to bend more readily, without restricting luminal cross-sectional area, thereby improving ease of handling during surgery, without increasing stress on the points of attachment and fixation. The ring like nodal architecture of the invention also produces tubular structures with significantly more resistance to tearing or splitting in the horizontal direction, as compared to conventional non-reinforced fluoropolymer tubular articles.

For experimentation, an extrudate was prepared by blending PTFE resin (Fluon CD-123 obtained from ICI Americas) with "ISOPAR-H" odorless solvent (produced by Exxon Corporation) used as an extrusion aid at a level of 150 cc of solvent per pound of resin. The blend was compressed into a tubular billet, heated to 30° C., and extruded into a 6 mm I.D. and 7 mm O.D. tube in a ram extruder having a reduction ratio of about 149:1 in cross-sectional area from billet to the extruded tube. The volatile extrusion aid was removed by drying in a heated oven prior to stretching.

To demonstrate the advantages of bilateral stretching in accordance with the invention, samples of the tubular extrudate were then stretched various ways as discussed below.

METHOD 1

An apparatus was developed that allowed samples of the tubular extrudate to be stretched at controlled rates and temperatures. The apparatus consisted of two clamps for holding the tube, one clamp held fixed within the oven and another clamp attached to a chain drive coupled to a variable speed motor. The tube was stretched an amount equal to 50% of its original length at a rate of approximately 10% per second. The fixed and moveable ends were then inverted and the stretching step repeated. The stretch and inversion steps were repeated until the extrudate sample had been stretched to a final stretch ratio of three to one. The oven temperature was then raised to 370° C. for ten minutes while the samples were held clamped.

METHOD 2

An apparatus was developed that allowed both ends of the extrudate to be displaced simultaneously, at a controlled temperature and rate. The apparatus included two clamps independently mounted to two slide drive systems. Following mounting to the stretch apparatus, both sides of the sample were displaced simultaneously at equal speeds in opposite directions for a selected distance. The applied stretch rate using the combined displacements rates from each side was calculated to be approximately 10% per second. The final stretch ratio was approximately three to one.

METHOD 3

The apparatus described in Method 2 was used to displace each end of the extrudate sequentially. That is, first one end of the extrudate was held fixed while the other was displaced a given distance at a constant speed, then, without inverting the sample, the previously displaced end was held stationary while the formerly stationary end was displaced the same distance at the same speed. Again, the sample was stretched at a rate of approximately 10% per second to a final ratio of approximately three to one.

Samples produced by the above described methods were then tested along with commercially available PTFE tubes produced by conventional, unilateral stretch techniques, the results appearing below.

| SAMPLE | A | B | C | D | E | F |
|---|---|---|---|---|---|---|
| Conventional | 3060 | 640 | 7.9 | 55 | 2.2 | 800 |
| Method 1 | 2660 | 803 | 2.9 | 90 | 0.5 | 1462 |
| Method 2 | 2720 | 833 | 2.8 | 95 | 0.5 | 1382 |
| Method 3 | 2400 | 845 | 2.8 | 95 | 0.5 | 1861 |

Where A is longitudinal tensile strength (pounds per square inch);

where B is radial tensile strength (pounds per square inch);

where C is water entry level (pounds per square inch);

where D is radial burst pressure (pounds per square inch);

where E is ethanol bubble point (pounds per square inch); and where F is suture strength (in grams) for a 2 mm bite.

Further, tubular extrudate samples as produced above were bilaterally stretched, displacing both ends simultaneously, at other stretch rates. Again, the stretch rates were calculated by combining the displacement rates of both ends of the extrudate. Tests performed on samples produced in this manner yielded the results detailed below.

|  | A | B | C | D | F |
|---|---|---|---|---|---|
| 10%/sec | 2232 | 780 | 2.8 | 95 | 1838 |
| 5%/sec | 2144 | 933 | 2.4 | 90 | 1657 |
| 0.5%/sec | 2372 | 953 | 2.1 | 105 | 1612 |

The data clearly indicate that enhanced radial strength and suture strength along with a corresponding decrease in Water Entry Pressure and Ethanol Bubble Point, result from the inventive bilateral stretching process.

For purposes of evaluating homogeneity, additional tubular extrudate samples were marked at ½" spaced intervals using a permanent marker. The samples were mounted and stretched either unilaterally with one end held fixed throughout the stretching process or bilaterally in which both ends were displaced simultaneously. After stretching at rates equal to or lower than 10% per second the samples were sintered and analyzed by measuring the distance between the marks along the sample lengths. The results detailed below indicate that at low rates of stretch bilateral stretching produces a structure which is more uniform than unilaterally stretched products. That is, with the bilaterally stretched samples, each ½" inch segment stretched an amount comparable to all segments through the length of the sample. Each unilaterally stretched sample, on the other hand, stretched preferentially at its moving end.

| BILATERAL STRETCHING FINAL STRETCH LENGTH IN INCHES OF EACH SEGMENT | | | | |
|---|---|---|---|---|
| ORIGINAL DISTANCE | 10%/SEC | | 5%/SEC | |
| FROM MIDDLE (INCHES) | 3:1 RATIO | 4:1 RATIO | 3:1 RATIO | 4:1 RATIO |
| 2.0 | 1.375 | 1.75 | 1.25 | 1.75 |
| 1.5 | 1.375 | 1.875 | 1.5 | 2.0 |
| 1.0 | 1.375 | 1.875 | 1.375 | 2.0 |
| 0.5 | 1.5 | 1.875 | 1.5 | 1.875 |
| 0.5 | 1.5 | 1.75 | 1.5 | 1.875 |
| 1.0 | 1.5 | 2.0 | 1.5 | 2.0 |
| 1.5 | 1.5 | 2.0 | 1.375 | 1.875 |
| 2.0 | 1.5 | 1.75 | 1.5 | 2.0 |

It can be seen that at a rate of 10% per second, bilaterally stretching an extrudate to a ratio of 3:1 in accordance with the invention yields an achieved expansion factor that varies by under 10% along the length of the stretched extrudate. Bilaterally stretching to a 4:1 ratio at this rate yields a variation of less than 8%.

Bilaterally stretching at 5% per second yields similar uniformities in achieved expansion factor. Moreover, such variations as there are, appear to be distributed in a more spatially uniform way.

UNILATERAL STRETCHING
FINAL STRETCH LENGTH IN INCHES OF EACH SEGMENT

| ORIGINAL DISTANCE FROM FIXED END (INCHES) | 10%/SEC | | 5%/SEC | | 0.5%/SEC | |
| --- | --- | --- | --- | --- | --- | --- |
| | 3:1 RATIO | 4:1 RATIO | 3:1 RATIO | 4:1 RATIO | 3:1 RATIO | 4:1 RATIO |
| 0.5 | 1.25  | 1.375 | 1.0   | 0.5   | 0.875 | 0.75 |
| 1.0 | 1.125 | 1.5   | 1.0   | 0.5   | 0.875 | 0.75 |
| 1.5 | 1.0   | 1.75  | 1.0   | 0.875 | 0.875 | 0.75 |
| 2.0 | 1.125 | 1.875 | 1.125 | 1.5   | 1.0   | 1.0  |
| 2.5 | 1.375 | 2.25  | 1.25  | 1.875 | 1.375 | 1.75 |
| 3.0 | 1.625 | 2.375 | 1.5   | 3.5   | 1.875 | 3.5  |
| 3.5 | 2.125 | 2.75  | 2.125 | 4.0   | 2.25  | 4.0  |
| 4.0 | 2.875 | 2.75  | 2.375 | 4.0   | 2.625 | 4.25 |

These results show that with unilateral stretching at the above-noted rates and ratios, a far greater variation in achieved expansion results. In particular, the results show that at these rates and ratios, a unilaterally stretched sample stretches preferentially at its moving end.

Figure 4:
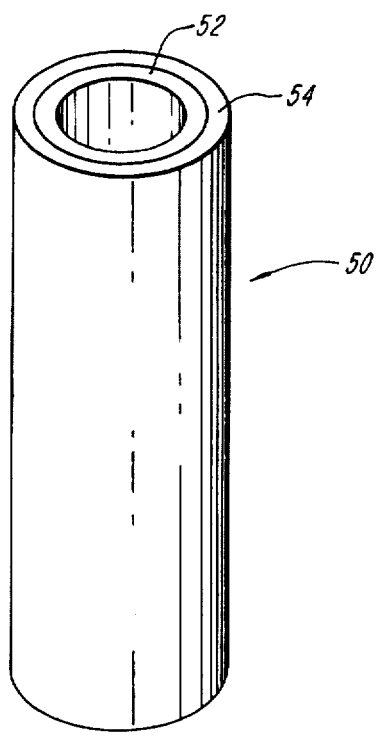
FIG. 4 is a schematic depiction of a billet suitable for extrusion in accordance with the invention.

In another embodiment of the invention, a porous article is formed utilizing a preformed billet such as billet 50 shown in FIG. 4. Billet 50 includes radial inner portion 52 and radial outer portion 54. A significant feature of billet 50 is that while radial portions 52 and 54 comprise the same resin, different levels of lubricant prevail in the portions.

The formation of layered preform billets is generally known in the art. For example, various known techniques have been used to produce extrudates having a conductive layer in electronic applications or a colored layer in general tubing applications. U.S. Pat. No. 4,973,609 assigned to Browne describes a layering technique using different resins.

In accordance with the invention, the microstructure of an extruded and expanded PTFE article is controlled using one resin with varying lube levels through the preform billet. For instance, the sample shown in FIGS. 5A through 5C was produced using a single PTFE resin that was preformed in a layer fashion at two different lube levels and processed according to the above described bilateral stretching process.

Figure 5A:
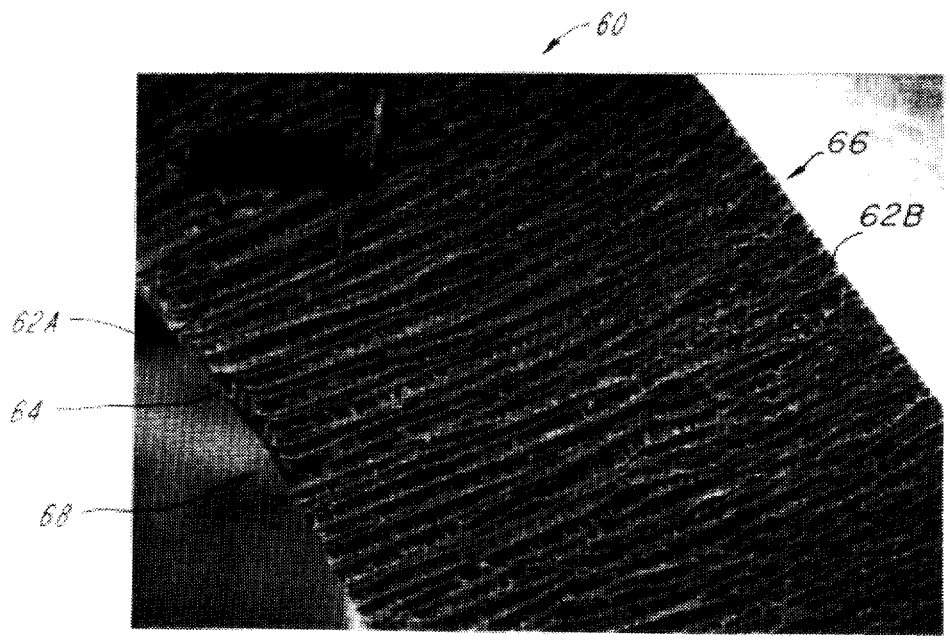
FIG. 5A is a scanning electron microscope longitudinal cross-section view of another porous article in accordance with the invention.
Figure 5B:
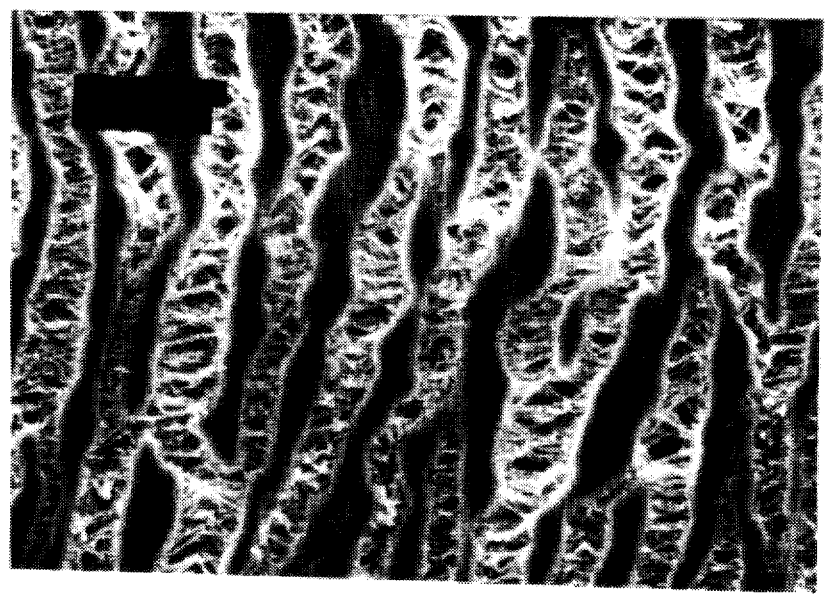
FIG. 5B is a scanning electron microscope view of the inner surface of the porous article shown in FIG. 5A.
Figure 5C:
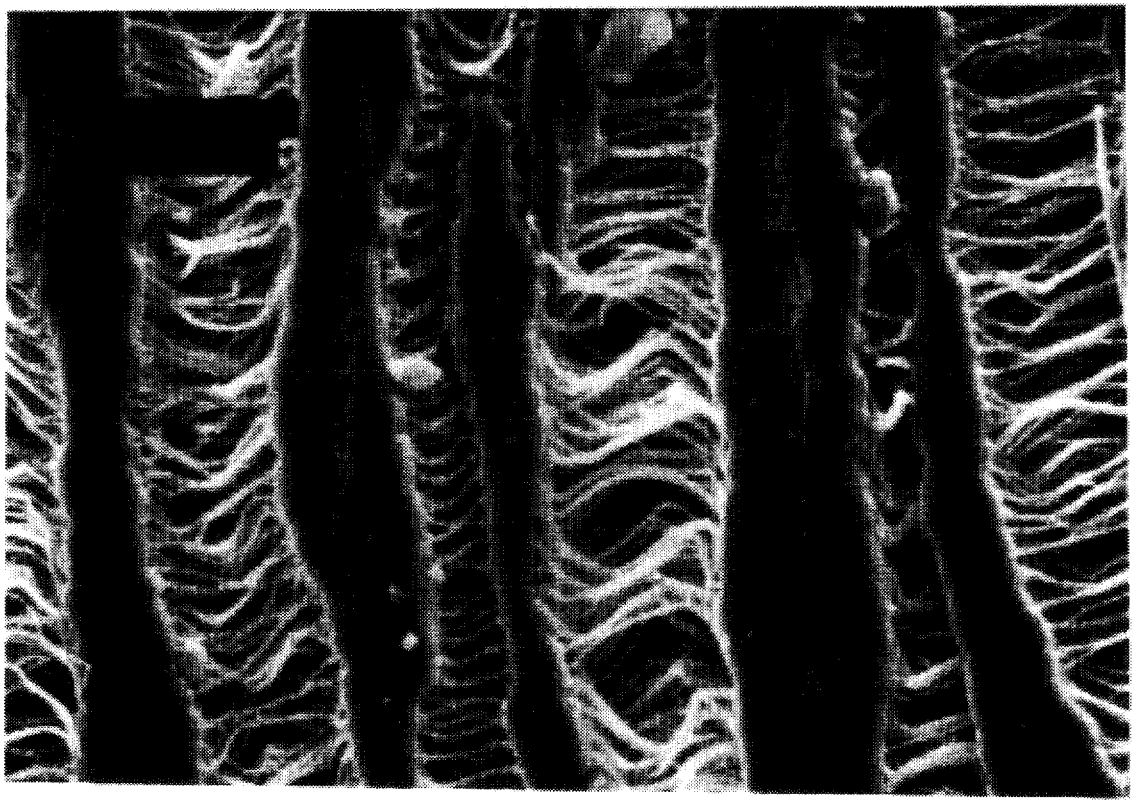
FIG. 5C is a scanning electron microscope view of the outer surface of the porous article shown in FIG. 5A.

FIG. 5A is a longitudinal cross-section view of a wall 60 of a tubular article formed utilizing the billet 50 in accordance with the above-described inventive process. As can be seen in the Figure, the material forming the wall 60 is characterized by a microstructure of large nodes 62A and small nodes 62B interconnected by fibrils 64. This results due to the inner radial portion 52 of billet 50 having a lower lubricant level than the outer radial portion 54. That is, lower lubricant levels result in smaller, more closely spaced nodes.

Several advantages accrue from the structure of wall 60. For example, by forming a tube having porosity at an inner surface 66 (FIG. 5B) which is smaller than the porosity at an outer surface 68 (FIG. 5C), a vascular graft is provided which defines an efficient flow channel at its inner surface while fostering improved cellular ingrowth at its outer surface.

Figure 6:
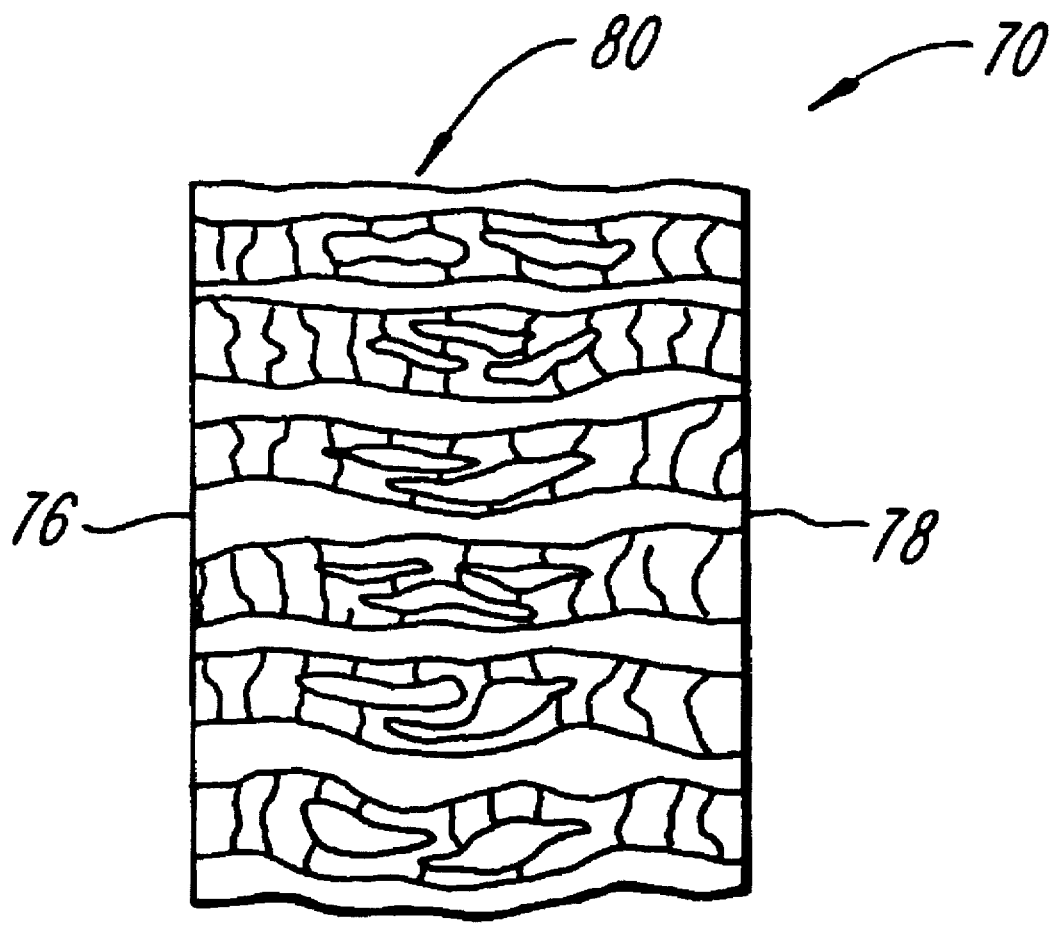
FIG. 6 is a schematic longitudinal cross-section view of still another porous article in accordance with the invention.

It should be understood that in addition to the illustrated embodiment, billets can be formed in accordance with the present invention having lubricant levels which vary in a selected pattern through the cross-section to achieve desired pore or channel distribution. Accordingly, by forming a tubular billet which has a lubricant level which is different at a radial position of the cross-section from the lubricant level at the inner and outer surfaces of the cross-section, a unique product is formed. For example, a tubular article having a wall 70, such as shown in FIG. 6, can be formed by this method. Note that the wall 70 has relatively large pores at its inner and outer surfaces 76 and 78 but includes a barrier region 80 of smaller pores between the inner and outer surfaces. Such a structure used as an implant or vascular graft is expected to promote cellular ingrowth from both sides of the wall 70 while preventing cellular growth completely through the wall.

For biological applications, the unique through-pore orientation created by the individual nodal spaces is exploited, for example, to either increase or decrease the migration of certain cellular and or biological materials directly into or onto the inventive tubular structure. This results in improved biocompatibility. For example, it is well documented that specific cell types penetrate, grow into, or onto porous fluoropolymer structures. By providing a matrix of large, oriented nodes to present non-tortuous pathways, full cellular penetration is possible, without "dead ended" channels. This offers a significantly improved cellular event. The provision of large-entry channels with a taper offers similar advantages, with the added feature of precisely limiting the depth of tissue penetration. Hence the hybrid nodal structure design of this invention offers many structural, physical and biological characteristics not found with other, well documented fluoropolymer process tubular articles.

In accordance with the invention, therefore, methods and materials are provided for the formation of biological implants having enhanced structures and tissue support features. Both organ wall grafts and vessel implants can be formed by practice of the invention.

Other alterations to the above described embodiments of the invention will be readily apparent to those skilled in the art and are intended, therefore, to be embraced within the spirit and scope of the invention. That is, the preceding detailed description is intended as illustrative rather than limiting. Accordingly, the invention is to be defined not by the preceding detailed description but by the claims that follow.

What is claimed is:

1. An implantable article formed by a wall of material extending in a thickness dimension front an inner face to an outer face and said wall consisting of a single expanded polytetrafluoroethylene (PTFE) material characterized in having a microstructure of a plurality of nodes interconnected by fibrils extending between the nodes, wherein internode spaces which are formed between pairs of adjacent nodes define oriented microchannels for passage of material therealong, wherein the microchannels are tapered and extend along the thickness dimension of the wall.

2. An implantable article according to claim 1, wherein the article is intended as a prosthesis and has a node and fibril microstructure that supports tissue growth, and the tapered microchannels taper outwardly to a wall on which tissue is to be grown.

3. A tube consisting of a single expanded, porous fluoropolymer material and having a longitudinal axis and a wall, the wall of said tube having a microstructure characterized by nodes being interconnected by fibrils, substantially all of the nodes each being disposed in annular region across the longitudinal axis of the tube and oriented such that space between adjacent nodes forms a channel oriented and extending in said region from the inner to the outer surface of the wall.

4. A tube as set forth in claim 3 wherein the fluoropolymer material comprises polytetrafluoroethylene.

5. A tube as set forth in claim 3 wherein the fluoropolymer material comprises a copolymer of tetrafluoroethylene and a monomer selected from the group consisting of ethylene, chlorotrifluoroethylene, perfluoroalkoxytetrafluoroethylene, and fluorinated propylenes.

6. A tube as set forth in claim 3 wherein the nodes are characterized by a dimension in a direction transverse to the longitudinal axis ranging from approximately 500 micrometers to approximately 900 micrometers.

7. A tube as set forth in claim 3 wherein the nodes define internodal through-pores, the through-pores providing substantially direct passageways which traverse from one surface of the tube to another.

8. A tube as set forth in claim 3 wherein said microstructure is substantially uniform along said longitudinal axis.

9. A tube consisting of a single expanded, porous fluoropolymer material and having a longitudinal axis and a wall, the wall of said tube having a microstructure characterized by ring-shaped nodes interconnected by fibrils, wherein a substantial plurality of the ring-shaped nodes each extend about the longitudinal axis of the tube, the ring-shaped nodes being sized and oriented such that space between a pair of adjacent nodes constitutes a channel oriented and extending in a radial direction, the wall further having a microstructure characterized by a second group of nodes smaller than the ring-shaped nodes and located along a radial region extending partway through the wall.

10. A tube as set forth in claim 9 wherein the nodes define internodal through-pores, the through-pores providing substantially direct passageways which traverse from one surface of the tube to another.

11. A tube as set forth in claim 9 wherein the ring shaped nodes and the second group of nodes define passageways having a size distribution that varies along a radial direction through the wall for controlling the extent of tissue ingrowth.

12. A tube as set forth in claim 9 wherein the fluoropolymer material comprises polytetrafluoroethylene.

13. A tube as set forth in claim 12 wherein the fluoropolymer material comprises a copolymer of tetrafluoroethylene and a monomer selected from the group consisting of ethylene, chlorotrifluoroethylene, perfluoroalkoxytetrafluoroethylene, and fluorinated propylenes.

14. A tube according to claim 9 wherein said micro structure is substantially uniform along the axis and varies along a radial direction through the wall.

15. A tube having a central axis and consisting of a single expanded porous polytetrafluoroethylene material, said tube having a microstructure of nodes interconnected by fibrils, substantially all of the nodes having plate shape oriented perpendicular to the central axis and extending between approximately five hundred and nine hundred microns in a plane perpendicular to said axis, said fibrils extending parallel to said axis, such that space between each pair of adjacent nodes forms a channel oriented and extending in said plane perpendicular to said axis.

16. A tube having a central axis and consisting of a single expanded porous polytetrafluoroethylene material, said tube being stretched along said axis to form a microstructure of nodes interconnected by fibrils and characterized by an expansion ratio defined along its length as a ratio of stretched length to initial length, wherein the expansion ratio varies by less than ten percent along the length of the tube and substantially all of the nodes are plates oriented perpendicular to the central axis and extending between approximately five hundred and nine hundred microns in a plane perpendicular to said axis, said fibrils extending parallel to said axis, such that space between a pair of adjacent nodes forms a channel oriented and extending through the tube in said plane perpendicular to said axis.

17. A tube according to claim 16 wherein the expansion ratio varies by less than about 1:16 over a substantial preponderance of the tube's length.

18. A tube having a central axis and consisting of a single expanded porous polytetrafluoroethylene material, said tube having a microstructure of nodes interconnected by fibrils wherein individual nodes extend from an inner surface to an outer surface of the tube and define large-entry channels for enhancing tissue ingrowth, the channels having said fibrils therein and having one porosity at the inner surface and a different porosity at the outer surface, the inner surface and the outer surface consisting of a single polytetrafluoroethylene material.

19. An implantable prosthesis having a body formed by a wall consisting of a single polytetrafluoroethylene (PTFE) material and having a first face and a second face, the PTFE material being stretched to impart a node and fibril structure wherein the nodes are plates extending entirely through the wall such that pairs of adjacent nodes each form a direct channel therebetween oriented and extending from said first face to said second face, the channels being large-entry channels to enhance tissue ingrowth at one of said first or second faces, and containing fibrils extending perpendicular to said nodes.

* * * * *

UNITED STATES PATENT AND TRADEMARK OFFICE
CERTIFICATE OF CORRECTION

PATENT NO. : 5,474,824
DATED : December 12, 1995
INVENTOR(S) : Paul Martakos et al.

It is certified that error appears in the above-indentified patent and that said Letters Patent is hereby corrected as shown below:

At column 12, line 64, please replace "dimension front" with --dimension from--.

Signed and Sealed this

Seventh Day of October, 1997

BRUCE LEHMAN

*Attest:*

*Attesting Officer*         Commissioner of Patents and Trademarks